US009616576B2

(12) United States Patent
Roe et al.

(10) Patent No.: US 9,616,576 B2
(45) Date of Patent: *Apr. 11, 2017

(54) MOBILE TELE-PRESENCE SYSTEM WITH A MICROPHONE SYSTEM

(71) Applicant: INTOUCH TECHNOLOGIES, INC., Goleta, CA (US)

(72) Inventors: David Bjorn Roe, Santa Barbara, CA (US); Daniel Steven Sanchez, Summerland, CA (US); Marco Pinter, Goleta, CA (US); Derek Walters, Campbell, CA (US); Charles S. Jordan, Santa Barbar, CA (US)

(73) Assignee: INTOUCH TECHNOLOGIES, INC., Goleta, CA (US)

(*) Notice: Subject to any disclaimer, the term of this patent is extended or adjusted under 35 U.S.C. 154(b) by 76 days.

This patent is subject to a terminal disclaimer.

(21) Appl. No.: 14/483,049

(22) Filed: Sep. 10, 2014

(65) Prior Publication Data

US 2015/0012136 A1    Jan. 8, 2015

Related U.S. Application Data

(63) Continuation of application No. 13/432,418, filed on Mar. 28, 2012, now Pat. No. 8,861,750, which is a
(Continued)

(51) Int. Cl.
*B25J 13/00* (2006.01)
*B25J 9/00* (2006.01)
(Continued)

(52) U.S. Cl.
CPC ........... *B25J 13/003* (2013.01); *B25J 9/0003* (2013.01); *B25J 19/023* (2013.01); *G06F 19/3418* (2013.01)

(58) Field of Classification Search
CPC ...... B25J 19/023; B25J 13/003; B25J 9/0003; G06F 19/3418
(Continued)

(56) References Cited

U.S. PATENT DOCUMENTS 4,107,689 A    8/1978  Jellinek
4,213,182 A    7/1980  Eichelberger et al.
(Continued)

FOREIGN PATENT DOCUMENTS

AU    1216200 A    5/2000
CN    1404695 A    3/2003
(Continued)

OTHER PUBLICATIONS

Fulbright et al., "SWAMI: An Autonomous Mobile Robot for Inspection of Nuclear Waste of Storage Facilities", Autonomous Robots, vol. 2, 1995, pp. 225-235.
(Continued)

*Primary Examiner* — Melur Ramakrishnaiah

(57) ABSTRACT

A remote controlled robot system that includes a robot and a remote control station. The robot includes a binaural microphone system that is coupled to a speaker system of the remote control station. The binaural microphone system may include a pair of microphones located at opposite sides of a robot head. the location of the microphones roughly coincides with the location of ears on a human body. Such microphone location creates a mobile robot that more effectively simulates the tele-presence of an operator of the system. The robot may include two different microphone systems and the ability to switch between systems. For example, the robot may also include a zoom camera system and a directional microphone. The directional microphone
(Continued)

may be utilized to capture sound from a direction that corresponds to an object zoomed upon by the camera system.

18 Claims, 3 Drawing Sheets

Related U.S. Application Data continuation of application No. 12/148,464, filed on Apr. 17, 2008, now Pat. No. 8,170,241.

(51) Int. Cl.
*B25J 19/02* (2006.01)
*G06F 19/00* (2011.01)

(58) Field of Classification Search
USPC .................. 381/113, 122; 348/14.01–14.09; 700/248, 245, 247, 251, 257, 258, 259
See application file for complete search history.

(56) References Cited

U.S. PATENT DOCUMENTS

| | | |
|---|---|---|
| 4,553,309 A | 11/1985 | Hess et al. |
| 4,679,152 A | 7/1987 | Perdue |
| 4,697,278 A | 9/1987 | Fleischer |
| 4,709,265 A | 11/1987 | Silverman et al. |
| 4,878,501 A | 11/1989 | Shue |
| 5,220,263 A | 6/1993 | Onishi et al. |
| 5,230,023 A | 7/1993 | Nakano |
| 5,262,944 A | 11/1993 | Weisner et al. |
| 5,347,306 A | 9/1994 | Nitta |
| 5,375,195 A | 12/1994 | Johnston |
| 5,400,068 A | 3/1995 | Ishida et al. |
| 5,413,693 A | 5/1995 | Redepenning |
| 5,436,542 A | 7/1995 | Petelin et al. |
| 5,511,147 A | 4/1996 | Abdel-Malek |
| 5,563,998 A | 10/1996 | Yaksich et al. |
| 5,617,539 A | 4/1997 | Ludwig et al. |
| 5,619,341 A | 4/1997 | Auyeung et al. |
| 5,623,679 A | 4/1997 | Rivette et al. |
| 5,675,229 A | 10/1997 | Thorne |
| 5,734,805 A | 3/1998 | Isensee et al. |
| 5,748,629 A | 5/1998 | Caldara et al. |
| 5,754,631 A | 5/1998 | Cave |
| 5,758,079 A | 5/1998 | Ludwig et al. |
| 5,787,545 A | 8/1998 | Colens |
| 5,793,365 A | 8/1998 | Tang et al. |
| 5,801,755 A | 9/1998 | Echerer |
| 5,844,599 A | 12/1998 | Hildin |
| 5,867,494 A | 2/1999 | Krishnaswamy et al. |
| 5,872,922 A | 2/1999 | Hogan et al. |
| 5,961,446 A | 10/1999 | Beller et al. |
| 5,995,119 A | 11/1999 | Cosatto et al. |
| 6,031,845 A | 2/2000 | Walding |
| 6,091,219 A | 7/2000 | Maruo et al. |
| 6,113,343 A | 9/2000 | Goldenberg et al. |
| 6,160,582 A | 12/2000 | Hill |
| 6,189,034 B1 | 2/2001 | Riddle |
| 6,233,735 B1 | 5/2001 | Ebihara |
| 6,250,928 B1 | 6/2001 | Poggio et al. |
| 6,292,714 B1 | 9/2001 | Okabayashi |
| 6,314,631 B1 | 11/2001 | Pryor |
| 6,317,652 B1 | 11/2001 | Osada |
| 6,317,953 B1 | 11/2001 | Pryor |
| 6,324,184 B1 | 11/2001 | Hou et al. |
| 6,324,443 B1 | 11/2001 | Kurakake et al. |
| 6,330,486 B1 * | 12/2001 | Padula ................... G06F 3/011 381/306 |
| 6,373,855 B1 | 4/2002 | Downing et al. |
| 6,389,329 B1 | 5/2002 | Colens |
| 6,411,055 B1 | 6/2002 | Fujita et al. |
| 6,445,964 B1 | 9/2002 | White et al. |
| 6,470,235 B2 | 10/2002 | Kasuga et al. |
| 6,480,762 B1 | 11/2002 | Uchikubo et al. |
| 6,529,620 B2 | 3/2003 | Thompson |
| 6,567,038 B1 | 5/2003 | Granot et al. |
| 6,590,604 B1 | 7/2003 | Tucker et al. |
| 6,597,392 B1 | 7/2003 | Jenkins et al. |
| 6,643,496 B1 | 11/2003 | Shimoyama et al. |
| 6,667,592 B2 | 12/2003 | Jacobs et al. |
| 6,674,259 B1 | 1/2004 | Norman et al. |
| 6,693,585 B1 | 2/2004 | MacLeod |
| 6,724,823 B2 | 4/2004 | Rovati et al. |
| 6,816,192 B1 | 11/2004 | Nishikawa |
| 6,816,754 B2 | 11/2004 | Mukai et al. |
| 6,893,267 B1 | 5/2005 | Yueh |
| 6,957,712 B2 | 10/2005 | Song et al. |
| 6,990,112 B1 | 1/2006 | Brent et al. |
| 7,007,235 B1 | 2/2006 | Hussein et al. |
| 7,011,538 B2 | 3/2006 | Chang |
| 7,015,934 B2 | 3/2006 | Toyama et al. |
| RE39,080 E | 4/2006 | Johnston |
| 7,053,578 B2 | 5/2006 | Diehl et al. |
| 7,055,210 B2 | 6/2006 | Keppler et al. |
| 7,158,861 B2 | 1/2007 | Wang et al. |
| 7,164,970 B2 | 1/2007 | Wang et al. |
| 7,167,448 B2 | 1/2007 | Wookey et al. |
| 7,171,286 B2 * | 1/2007 | Wang ..................... H04N 7/142 318/568.11 |
| 7,181,455 B2 | 2/2007 | Wookey et al. |
| 7,215,786 B2 * | 5/2007 | Nakadai ............. G10L 21/0208 318/568.12 |
| 7,219,364 B2 | 5/2007 | Bolle et al. |
| 7,222,000 B2 | 5/2007 | Wang et al. |
| 7,283,153 B2 | 10/2007 | Provost et al. |
| 7,292,257 B2 | 11/2007 | Kang et al. |
| 7,305,114 B2 | 12/2007 | Wolff et al. |
| 7,317,685 B1 | 1/2008 | Flott et al. |
| 7,332,890 B2 | 2/2008 | Cohen et al. |
| 7,333,642 B2 | 2/2008 | Green |
| 7,352,153 B2 | 4/2008 | Yan |
| 7,363,121 B1 | 4/2008 | Chen et al. |
| 7,400,578 B2 | 7/2008 | Guthrie et al. |
| 7,421,470 B2 | 9/2008 | Ludwig et al. |
| 7,430,209 B2 | 9/2008 | Porter |
| 7,433,921 B2 | 10/2008 | Ludwig et al. |
| 7,467,211 B1 | 12/2008 | Herman et al. |
| 7,483,867 B2 | 1/2009 | Ansari et al. |
| 7,492,731 B2 | 2/2009 | Hagendorf |
| 7,510,428 B2 | 3/2009 | Obata et al. |
| 7,523,069 B1 | 4/2009 | Friedl et al. |
| 7,557,758 B2 | 7/2009 | Rofougaran |
| 7,587,260 B2 | 9/2009 | Bruemmer et al. |
| 7,587,512 B2 | 9/2009 | Ta et al. |
| 7,590,060 B2 | 9/2009 | Miceli |
| 7,599,290 B2 | 10/2009 | Dos Remedios et al. |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,657,560 B1 | 2/2010 | DiRienzo |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 | 4/2010 | Dawson |
| 7,737,993 B2 | 6/2010 | Kaasila et al. |
| 7,739,383 B1 | 6/2010 | Short et al. |
| 7,756,614 B2 | 7/2010 | Jouppi |
| 7,769,705 B1 | 8/2010 | Luechtefeld |
| 7,774,158 B2 | 8/2010 | Domingues Goncalves et al. |
| 7,861,366 B2 | 1/2011 | Hahm et al. |
| 7,885,822 B2 | 2/2011 | Akers et al. |
| 7,890,382 B2 | 2/2011 | Robb et al. |
| 7,912,583 B2 | 3/2011 | Gutmann et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,982,769 B2 | 7/2011 | Jenkins et al. |
| 7,987,069 B2 | 7/2011 | Rodgers et al. |
| 8,126,960 B2 | 2/2012 | Obradovich et al. |
| 8,212,533 B2 | 7/2012 | Ota |
| 8,265,793 B2 | 9/2012 | Cross et al. |

(56) References Cited

U.S. PATENT DOCUMENTS

| | | |
|---|---|---|
| 8,287,522 B2 | 10/2012 | Moses et al. |
| 8,292,807 B2 | 10/2012 | Perkins et al. |
| 8,320,534 B2 | 11/2012 | Kim et al. |
| 8,340,654 B2 | 12/2012 | Bratton et al. |
| 8,340,819 B2 | 12/2012 | Mangaser et al. |
| 8,348,675 B2 | 1/2013 | Dohrmann |
| 8,374,171 B2 | 2/2013 | Cho et al. |
| 8,400,491 B1 | 3/2013 | Panpaliya et al. |
| 8,401,275 B2 | 3/2013 | Wang et al. |
| 8,423,284 B2 | 4/2013 | O'Shea |
| 8,451,731 B1 | 5/2013 | Lee et al. |
| 8,463,435 B2 | 6/2013 | Herzog et al. |
| 8,503,340 B1 | 8/2013 | Xu |
| 8,515,577 B2 | 8/2013 | Wang et al. |
| 8,527,094 B2 | 9/2013 | Kumar et al. |
| 8,532,860 B2 | 9/2013 | Daly |
| 8,610,786 B2 | 12/2013 | Ortiz |
| 8,612,051 B2 | 12/2013 | Norman et al. |
| 8,639,797 B1 | 1/2014 | Pan et al. |
| 8,670,017 B2 | 3/2014 | Stuart et al. |
| 8,726,454 B2 | 5/2014 | Gilbert et al. |
| 8,836,751 B2 | 9/2014 | Ballantyne et al. |
| 8,849,679 B2 | 9/2014 | Wang et al. |
| 8,849,680 B2 | 9/2014 | Wright et al. |
| 8,897,920 B2 | 11/2014 | Wang et al. |
| 8,902,278 B2 | 12/2014 | Pinter et al. |
| 2001/0020200 A1 | 9/2001 | Das et al. |
| 2001/0048464 A1 | 12/2001 | Barnett |
| 2002/0027652 A1 | 3/2002 | Paromtchik et al. |
| 2002/0033880 A1 | 3/2002 | Sul et al. |
| 2002/0038168 A1 | 3/2002 | Kasuga et al. |
| 2002/0044201 A1 | 4/2002 | Alexander et al. |
| 2002/0095239 A1 | 7/2002 | Wallach et al. |
| 2002/0106998 A1 | 8/2002 | Presley et al. |
| 2002/0109775 A1 | 8/2002 | White et al. |
| 2002/0128985 A1 | 9/2002 | Greenwald |
| 2002/0133062 A1 | 9/2002 | Arling et al. |
| 2003/0021107 A1 | 1/2003 | Howell et al. |
| 2003/0050734 A1 | 3/2003 | Lapham |
| 2003/0080901 A1 | 5/2003 | Piotrowski |
| 2003/0112823 A1 | 6/2003 | Collins et al. |
| 2003/0120714 A1 | 6/2003 | Wolff et al. |
| 2003/0135097 A1 | 7/2003 | Wiederhold et al. |
| 2003/0152145 A1 | 8/2003 | Kawakita |
| 2003/0195662 A1 | 10/2003 | Wang et al. |
| 2003/0212472 A1 | 11/2003 | McKee |
| 2003/0216833 A1 | 11/2003 | Mukai et al. |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0008138 A1 | 1/2004 | Hockley, Jr. et al. |
| 2004/0017475 A1 | 1/2004 | Akers et al. |
| 2004/0088078 A1 | 5/2004 | Jouppi et al. |
| 2004/0095516 A1 | 5/2004 | Rohlicek |
| 2004/0107254 A1 | 6/2004 | Ludwig et al. |
| 2004/0107255 A1 | 6/2004 | Ludwig et al. |
| 2004/0117067 A1 | 6/2004 | Jouppi |
| 2004/0123158 A1 | 6/2004 | Roskind |
| 2004/0150725 A1 | 8/2004 | Taguchi |
| 2004/0168148 A1 | 8/2004 | Goncalves et al. |
| 2004/0172306 A1 | 9/2004 | Wohl et al. |
| 2004/0186623 A1 | 9/2004 | Dooley et al. |
| 2004/0218099 A1 | 11/2004 | Washington |
| 2004/0240981 A1 | 12/2004 | Dothan et al. |
| 2004/0260790 A1 | 12/2004 | Balloni et al. |
| 2005/0004708 A1 | 1/2005 | Goldenberg et al. |
| 2005/0060211 A1 | 3/2005 | Xiao et al. |
| 2005/0073575 A1 | 4/2005 | Thacher et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0168568 A1 | 8/2005 | Jouppi |
| 2005/0231586 A1 | 10/2005 | Rodman et al. |
| 2005/0234592 A1 | 10/2005 | McGee et al. |
| 2005/0264649 A1 | 12/2005 | Chang et al. |
| 2005/0286759 A1 | 12/2005 | Zitnick et al. |
| 2006/0010028 A1 | 1/2006 | Sorensen |
| 2006/0014388 A1 | 1/2006 | Lur et al. |
| 2006/0056655 A1 | 3/2006 | Wen et al. |
| 2006/0056837 A1 | 3/2006 | Vapaakoski |
| 2006/0066609 A1 | 3/2006 | Iodice et al. |
| 2006/0071797 A1 | 4/2006 | Rosenfeld et al. |
| 2006/0125356 A1 | 6/2006 | Meek, Jr. et al. |
| 2006/0149418 A1 | 7/2006 | Anvari |
| 2006/0161136 A1 | 7/2006 | Anderson et al. |
| 2006/0171515 A1 | 8/2006 | Hintermeister et al. |
| 2006/0173708 A1 | 8/2006 | Vining et al. |
| 2006/0178559 A1 | 8/2006 | Kumar et al. |
| 2006/0178777 A1 | 8/2006 | Park et al. |
| 2006/0224781 A1 | 10/2006 | Tsao et al. |
| 2006/0247045 A1 | 11/2006 | Jeong et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2007/0025711 A1 | 2/2007 | Marcus |
| 2007/0093279 A1 | 4/2007 | Janik |
| 2007/0116152 A1 | 5/2007 | Thesling |
| 2007/0133407 A1 | 6/2007 | Choi et al. |
| 2007/0170886 A1 | 7/2007 | Plishner |
| 2007/0198130 A1 | 8/2007 | Wang et al. |
| 2007/0226949 A1 | 10/2007 | Hahm et al. |
| 2007/0255706 A1 | 11/2007 | Iketani et al. |
| 2007/0290040 A1 | 12/2007 | Wurman et al. |
| 2008/0009969 A1 | 1/2008 | Bruemmer et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'Andrea et al. |
| 2008/0086241 A1 | 4/2008 | Phillips et al. |
| 2008/0091340 A1 | 4/2008 | Milstein et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0232763 A1 | 9/2008 | Brady |
| 2008/0263628 A1 | 10/2008 | Norman et al. |
| 2008/0267069 A1 | 10/2008 | Thielman et al. |
| 2008/0306375 A1 | 12/2008 | Sayler et al. |
| 2009/0044334 A1 | 2/2009 | Parsell et al. |
| 2009/0049640 A1 | 2/2009 | Lee et al. |
| 2009/0086013 A1 | 4/2009 | Thapa |
| 2009/0102919 A1 | 4/2009 | Zamierowski et al. |
| 2009/0106679 A1 | 4/2009 | Anzures et al. |
| 2009/0122699 A1 | 5/2009 | Alperovitch et al. |
| 2009/0144425 A1 | 6/2009 | Marr et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0248200 A1 | 10/2009 | Root |
| 2010/0017046 A1 | 1/2010 | Cheung et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0066804 A1 | 3/2010 | Shoemake et al. |
| 2010/0085874 A1 | 4/2010 | Noy et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0228249 A1 | 9/2010 | Mohr et al. |
| 2010/0278086 A1 | 11/2010 | Pochiraju et al. |
| 2010/0286905 A1 | 11/2010 | Goncalves et al. |
| 2010/0301679 A1 | 12/2010 | Murray et al. |
| 2011/0022705 A1 | 1/2011 | Yellamraju et al. |
| 2011/0071675 A1 | 3/2011 | Wells et al. |
| 2011/0072114 A1 | 3/2011 | Hoffert et al. |
| 2011/0153198 A1 | 6/2011 | Kokkas et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |
| 2011/0280551 A1 | 11/2011 | Sammon |
| 2011/0306400 A1 | 12/2011 | Nguyen |
| 2012/0036484 A1 | 2/2012 | Zhang et al. |

(56) References Cited

U.S. PATENT DOCUMENTS

| | | | |
|---|---|---|---|
| 2012/0059946 | A1 | 3/2012 | Wang |
| 2012/0072024 | A1 | 3/2012 | Wang et al. |
| 2012/0095352 | A1 | 4/2012 | Tran |
| 2012/0113856 | A1 | 5/2012 | Krishnaswamy |
| 2012/0191464 | A1 | 7/2012 | Stuart et al. |
| 2012/0203731 | A1 | 8/2012 | Nelson et al. |
| 2012/0291809 | A1 | 11/2012 | Kuhe et al. |
| 2013/0250938 | A1 | 9/2013 | Anandakumar et al. |
| 2014/0047022 | A1 | 2/2014 | Chan et al. |
| 2014/0085543 | A1 | 3/2014 | Hartley et al. |
| 2014/0135990 | A1 | 5/2014 | Stuart et al. |
| 2014/0139616 | A1 | 5/2014 | Pinter et al. |
| 2014/0155755 | A1 | 6/2014 | Pinter et al. |

FOREIGN PATENT DOCUMENTS

| | | | |
|---|---|---|---|
| CN | 1561923 | A | 1/2005 |
| CN | 1743144 | A | 3/2006 |
| CN | 101049017 | A | 10/2007 |
| CN | 101151614 | A | 3/2008 |
| CN | 100407729 | C | 7/2008 |
| EP | 1304872 | A1 | 4/2003 |
| EP | 1763243 | A2 | 3/2007 |
| EP | 1819108 | A2 | 8/2007 |
| EP | 1232610 | B1 | 1/2009 |
| GB | 2431261 | A | 4/2007 |
| JP | 07194609 | A | 8/1995 |
| JP | 11220706 | A | 8/1999 |
| JP | 2002321180 | A | 11/2002 |
| JP | 2004181229 | A | 7/2004 |
| JP | 2005111083 | A | 4/2005 |
| JP | 2007007040 | A | 1/2007 |
| JP | 2007232208 | A | 9/2007 |
| JP | 2007316966 | A | 12/2007 |
| JP | 2009125133 | A | 6/2009 |
| WO | 9742761 | A1 | 11/1997 |
| WO | 0025516 | A1 | 5/2000 |
| WO | 0131861 | A1 | 5/2001 |
| WO | 2009145958 | A2 | 12/2009 |

OTHER PUBLICATIONS

"Appeal from the U.S. District Court for the Central District of California in case No. 11-cv-9185, Judge Percy Anderson, Joint Appendix, vol. I of IV", Jun. 24, 2013, pp. A1-A6357.
"Appeal from the U.S. District Court for the Central District of California in case No. 11-cv-9185, Judge Percy Anderson, Joint Appendix, vol. II of IV", Jun. 24, 2013, pp. A6849-A10634.
"Appeal from the U.S. District Court for the Central District of California in case No. 11-cv-9185, Judge Percy Anderson, Joint Appendix, vol. III of IV", Jun. 24, 2013, pp. A10654-A15517.
"Appeal from the U.S. District Court for the Central District of California in case No. 11-cv-9185, Judge Percy Anderson, Joint Appendix, vol. IV of IV", Jun. 24, 2013, pp. A15677-A18127.
"Appeal from the U.S. District Court for the Central District of California in No. 11-CV-9185, Judge Percy Anderson", May 9, 2014, pp. 1-48.
"Civil Minutes-General: Case No. CV 11-9185PA (AJWx), InTouch Tech., Inc. v. VGO Commons, Inc.", Sep. 10, 2012, 7 pages.
"Google translation of: Innovations Report", From research project to television star: Care-O-bot in ZDF series, http://www.innovations-report.de/specials/printa.php?id=5157, Sep. 28, 2001, 2 pages.
"Magne Charge", Smart Power for Electric Vehicles, Aug. 26, 1997, 2 pages.
"MPEG File Format Summary", downloaded from: http://www.fileformat.info/format/mpeg/egff.htm, Feb. 1, 2001, 8 pages.
"Nomad Scout User's Manual", Nomadic Technologies, Software Version 2. 7, Part No. DOC00004, Jul. 12, 1999, pp. 1-59.
"Opening Brief for Plaintiff-Appellant InTouch Technologies, Inc., Appeal from the U.S. District Court for the Central District of California in Case No. 11-cv-9185, Judge Percy Anderson", Apr. 12, 2013, 187 pages.
"Reply Brief for Defendant-Appellee VGO Communications, Inc., Appeal from the U.S. District Court for the Central District of California, in Case No. 2:11-cv-9185, Judge Percy Anderson", May 28, 2013, 75 pages.
"Reply Brief for Plaintiff-Appellant InTouch Technologies, Inc., Appeal from the U.S. District Court for the Central District of California in Case No. 11-cv-9185, Judge Percy Anderson", Jun. 14, 2013, 39 pages.
"Using your Infrared Cell Phone Camera", http://www.catsdomain.com/xray/about.htm, Courtesy of Internet Wayback Machine, Jan. 30, 2010, 4 pages.
Office Action Received for Chinese Patent Application No. 200680044698.0, issued Nov. 4, 2010, 26 pages.
ACM Digital Library Record, "Autonomous Robots vol. 11 Issue 1", downloaded from <http://dl.acm.org/citation.cfm?id=591550&picked=prox&cfid=360891374&cftoken=35225929>, Jul. 2001, 2 pages.
Activemedia, Inc.,, "Saphira Software Manual", Saphira Version 5.3, ActiveMedia, Inc., 1997, 105 pages.
Activmedia Robotics, "Pioneer 2/PeopleBot TM", Operations Manual , Version 9, Oct. 2001, 78 pages.
Adams, "Simulation of Adaptive Behavior (SAB'02)", Mobile Robotics Research Group, The Seventh International Conference, retrieved on Jan. 22, 2014, available at: http://www.dai.ed.ac.uk/groups/mrg/MRG.html, Aug. 4-11, 2002, 1 page.
Apple Inc., "I Phone", iPhone Series, XP002696350, Sep. 21, 2012, pp. 1-29.
Bradner, "The Internet Standards Process—Revision 3", Network Working Group, Request for Comments: 2026, BCP: 9, Obsoletes: 1602, Category: Best Current Practice, Oct. 1996, pp. 1-36.
Brenner, "A technical tutorial on the IEEE 802.11 protocol", BreezeCOM Wireless Communications, 1997, pp. 1-24.
Christensen, et al., "BeeSoft User's Guide and Reference", Robots for the Real World™, Real World Interface, Inc ., Sep. 26, 1997, 203 pages.
CMU Course 16X62, "Robot user's manual", (describing the Nomad Scout), Carnegie Mellon University, Feb. 1, 2001, 11 pages.
Evans, et al., "The Trackless Robotic Courier", PYXIS HelpMate®, 3 pages.
Gaidioz, et al., "Synchronizing Network Probes to Avoid Measurement Intrusiveness with the Network Weather Service", Proceedings of the Ninth International Symposium on High-Performance Distributed Computing,, 2000, pp. 147-154.
Garner, et al., "The Application of Telepresence in Medicine", BT Technology Journal, vol. 15, No. 4, Oct. 1, 1997, pp. 181-187.
Goldenberg, et al., "Telemedicine in Otolaryngology", American Journal of Otolaryngology, vol. 23,No. 1, 2002, pp. 35-43.
Gostai, "Gostai Jazz: Robotic Telepresence", Available online at <http://www.gostai.com>, 4 pages.
Jacobs, et al., "Applying Telemedicine to Outpatient Physical Therapy", AMIA, Annual Symposium Proceedings, 2002, 1 page.
Koenen, "MPEG-4: a Powerful Standard for Use in Web and Television Environments", (KPN Research), downloaded from http://www.w3.org/Architecture/1998/06/Workshop/paper26, Jul. 1, 1998, 4 pages.
Kurlowicz, et al., "The Mini Mental State Examination (MMSE)", Try This: Best Practices in Nursing Care to Older Adults, A series from the Hartford Institute of Geriatric Nursing, Issue No. 3, Jan. 1999, 2 pages.
Leifer, et al., "VIPRR: A Virtually in Person Rehabilitation Robot", Proceedings of 1997 International Conference on Rehabilitation Robotics, Apr. 14-15, 1997, 4 pages.
Lemaire, "Using Communication Technology to Enhance Rehabilitation Services: A Solution Oriented User Manual", Institute for Rehabilitation Research and Development, Terry Fox Mobile Clinic, The Rehabilitation Centre, Ottawa, Ontario, Canada, Version 2.0; http://www.irrd.ca/telehealth/distfile/distman_v2_1.pdf, 1998-2001, 104 pages.
Library of Congress, "008—Fixed-Length Data Elements (NR)", MARC 21 Format for Classification Data, downloaded from http://www.loc.gov/marc/classification/cd008.html, Jan. 2000, pp. 1-14.
Minsky, "Telepresence", OMNI Magazine, Jun. 1980, 6 pages.

(56) References Cited

OTHER PUBLICATIONS

Nakazato, et al., "Group-Based Interface for Content-Based Image Retrieval", Proceedings of the Working Conference on Advanced Visual Interfaces, 2002, pp. 187-194.

Nakazato, et al., "ImageGrouper: A Group-Oriented User Interface for Content-Based Image Retrieval and Digital Image Arrangement", Journal of Visual Languages & Computing, vol. 14, No. 4, Aug. 2003, pp. 45-46.

North, "Telemedicine: Sample Script and Specifications for a Demonstration of Simple Medical Diagnosis and Treatment Using Live Two-Way Video on a Computer Network", Greenstar Corporation, 1998, 5 pages.

Osborn, "Quality of Life Technology Center", QoLT Research Overview:A National Science Foundation Engineering Research Center, Carnegie Mellon University of Pittsburgh, 2 pages.

Panusopone, et al., "Performance comparison of MPEG-4 and H.263+ for streaming video applications", Circuits Systems Signal Processing, vol. 20, No. 3, 2001, pp. 293-309.

Paulos, et al., "Personal Tele-Embodiment", Chapter 9 in Goldberg, et al., ed. "Beyond webcams", MIT Press, Jan. 4, 2002, pp. 155-167.

Paulos, "Personal tele-embodiment", OskiCat Catalog Record, UCB Library Catalog, 2001, 3 pages.

Paulos, "Personal Tele-Embodiment", Introductory and cover pages from 2001 Dissertation including Contents table, together with e-mails relating thereto from UC Berkeley Libraries, as shelved at UC Berkeley Engineering Library (Northern Regional library Facility), May 8, 2002, 25 pages, including 4 pages of e-mails.

Paulos, et al., "Social Tele-Embodiment: Understanding Presence", Autonomous Robots, vol. 11, Issue 1, Kluwer Academic Publishers, Jul. 2001, pp. 87-95.

Piquepaille, "This Blog and its RSS Feed are Moving", Roland Piquepaille's Technology Trends, How new technologies are modifying our way of life,, Oct. 31, 2004, 2 pages.

Radvision, "Making Sense of Bandwidth the NetsenseWay", Network Congestion in Unmanaged Networks Bandwidth Estimation and Adaptation Techniques,White Paper, Radvision's Netsense Technology, 2010, 7 pages.

Reynolds, et al., "Review of Robotic Telemedicine Utilization in Intensive Care Units (ICUs)", 11th Annual ATA Symposium, Tampa, Florida, 2011, 1 page.

Roy, et al., "Towards Personal Service Robots for the Elderly", Workshop on Interactive Robots and Entertainment (Wire 2000), vol. 25, http://www.ri.cmu.edu/pb_files/pub2/roy_nicholas_2000_1/roy_nicholas_2000_1.pdf, Apr. 30-May 1, 2000, 7 pages.

Schraft, et al., "Care-O-bot™: the concept of a system fro assisting elderly or disabled persons in home enviornments", IEEE Proceedings of the 24th Annual Conference of the Industrial Electronics Society, IECON '98, Aug. 31-Sep. 4, 1998, pp. 2476-2481.

Screenshot Showing Google Date for Lemaire Telehealth Manual, Screenshot Retrieved on Dec. 18, 2014, 1 page.

Nomadic Technologies, Inc., "Nomad Scout Language Reference Manual", Software Version: 2.7, Part No. DOC00002, Jul. 12, 1999, 47 pages.

Telepresence Research, Inc., "The Telepresence Mobile Robot System", Available at: http://www.telepresence.com/telepresence-research/TELEROBOT/, Retrieved on Nov. 23, 2010, Feb. 20, 1995, 3 pages.

Theodosiou et al., "MuLVAT: A Video Annotation Tool Based on XML-Dictionaries and Shot Clustering", Part II, 19th International Conference, Artificial Neural Networks-ICANN 2009, Sep. 14-17, 2009, pp. 913-922.

Tipsuwan, et al., "Gain Adaptation of Networked Mobile Robot to Compensate QoS Deterioration", 28th Annual Conference of the Industrial Electronics Society, vol. 4, Nov. 5-8, 2002, pp. 3146-3151.

Tsui et al., "Exploring Use Cases for Telepresence Robots", 6th ACM/IEEE International Conference on Human-Robot Interaction (HRI), Mar. 2011, pp. 11-18.

Tyrrell, et al., "Teleconsultation in Psychology: The Use of Videolinks for Interviewing and Assessing Elderly Patients", Age and Ageing, vol. 30, No. 3, May 2001, pp. 191-195.

UMASS Lowell Robotics Lab, "Robotics Lab @ UMASS Lowell", Brochure, 2011, 2 pages.

Video Middleware Cookbook, "H.350 Directory Services for Multimedia", Video Middleware Group, 2 pages.

Weaver et al., "Monitoring and Controlling Using the Internet and Java", Proceedings of the 25th Annual Conference of the IEEE Industrial Electronics Society, vol. 3, 1999, pp. 1152-1158.

* cited by examiner

MOBILE TELE-PRESENCE SYSTEM WITH A MICROPHONE SYSTEM

BACKGROUND OF THE INVENTION

1. Field of the Invention

The subject matter disclosed generally relates to the field of mobile two-way teleconferencing.

2. Background Information

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

Tele-robots such as hazardous waste handlers and bomb detectors may contain a camera that allows the operator to view the remote site. U.S. Pat. No. 6,914,622 issued to Smith et al. and assigned to Telbotics, Inc. ("Telbotics patent") discloses a teleconferencing platform that has both a camera and a monitor. The platform includes mechanisms to both pivot and raise the camera and the monitor. The Telbotics patent has a microphone and a system that automatically swivels the monitor to the origin of sound so that the user's image as displayed by the robot monitor faces a speaker.

There has been marketed a mobile robot introduced by InTouch Technologies, Inc., the assignee of this application, under the trademarks COMPANION and RP-7. The InTouch robot is controlled by a user at a remote station. The remote station may be a personal computer with a joystick that allows the user to remotely control the movement of the robot. Both the robot and remote station have cameras, monitors, speakers and microphones to allow for two-way video/audio communication. The robot camera provides video images to a screen at the remote station so that the user can view the robot's surroundings and move the robot accordingly. It would be desirable to create a microphone system that more closely simulated sound perceived by human errors so that the user experiences a more realistic auditory presence through the robot.

BRIEF SUMMARY OF THE INVENTION

A remote controlled robot system that includes a robot and a remote control station. The robot includes a monitor and a binaural microphone system. The remote control station includes a speaker system coupled to the binaural microphone system.

BRIEF DESCRIPTION OF THE DRAWINGS

FIG. 1A is an illustration showing the relationship of two microphones relative to a monitor of a robot head;

DETAILED DESCRIPTION

Disclosed is a remote controlled robot system that includes a robot and a remote control station. The robot includes a binaural microphone system that is coupled to a speaker system of the remote control station. The binaural microphone system may include a pair of microphones located at opposite sides of a robot head. The location of the microphones roughly coincides with the location of ears on a human body. Such microphone location provides the remote operator with a realistic auditory presence including directionality and distance, as if the operator were actually present at the robot location. The robot may include two different microphone systems and the ability to switch between systems. For example, the robot may also include a zoom camera system and a directional microphone. The directional microphone may be utilized to capture sound from a direction that corresponds to an object zoomed upon by the camera system.

Figure 1:
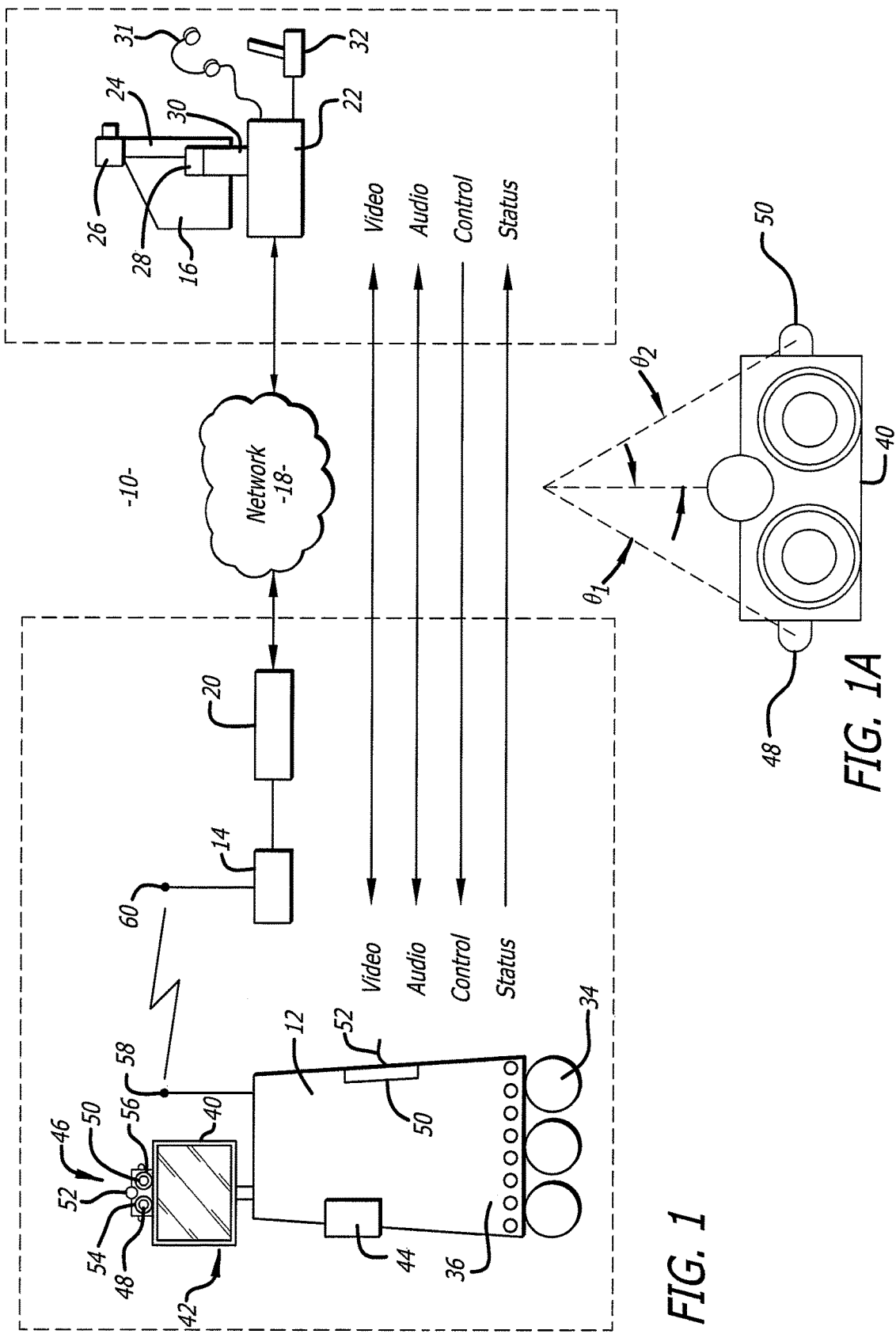
FIG. 1 is an illustration of a robotic system.

Referring to the drawings more particularly by reference numbers, FIG. 1 shows a robotic system 10 that can be used to conduct a remote visit. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network thru for example a satellite.

The remote control station 16 may include a computer 22 that has a monitor 24, a camera 26, a microphone 28 and a speaker 30. The station 16 may also include a headset 31 that can be worn by the user. The computer 22 may have an input device 32 such as a joystick and/or a mouse and a keyboard 33. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Figure 2:
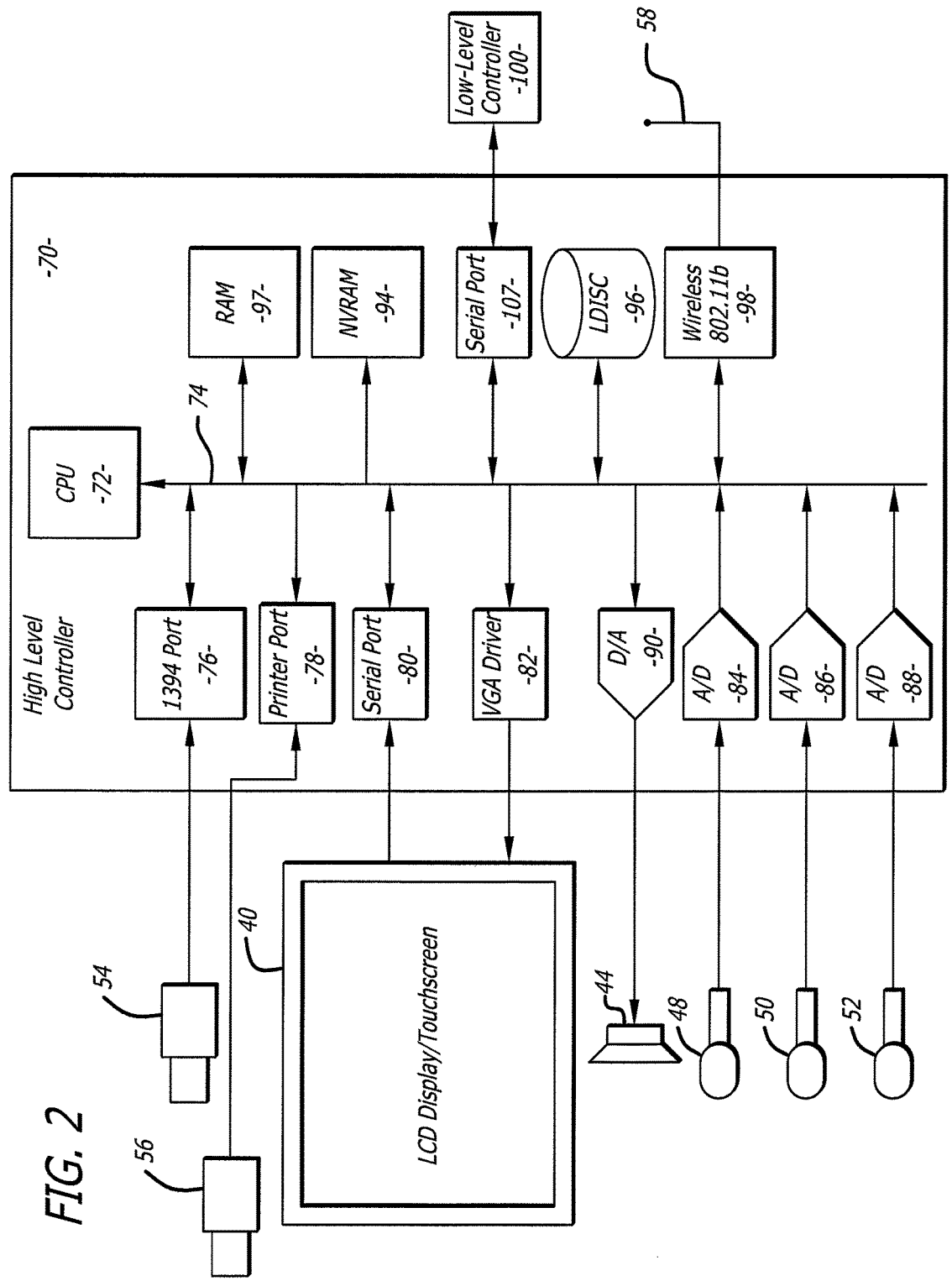
FIG. 2 is a schematic of an electrical system of a robot.

Each robot 12 includes a movement platform 34 that is attached to a robot housing 36. As shown in FIG. 2 each robot 12 may include a monitor 40 that display an image of the operator at the remote control station. The monitor 40 may be part of a robot head 42 that moves relative to the movement platform 34. The head 42 may have a speaker system 44 that generates sound provided by the remote control station.

The robot 12 includes a binaural microphone system 46. The binaural microphone system 46 includes a first microphone 48 located on one side of the head and a second microphone 50 located on another side of the head. The microphones 48 and 50 are located at positions approximately similar to the location of ears on a human body. By way of example, the microphones 48 and 50 can be located about 18 centimeters apart. Utilizing a binaural microphone system 46 creates a robot head that approximates a human head. By way of example, the binaural microphone system 46 may be a matched pair of omni-directional electric condenser microphones. One definition of binaural is that the microphones 48 and 50 are located at positions at approximately equal angles relative to a plane that intersects and is essentially perpendicular to the camera system which is incident with the monitor 40 as shown in FIG. 1A (e.g. $\theta_1 = \theta_2$).

A matched pair of microphones produce an equal voltage for a given sound pressure. The output signals of the microphones may be processed to produce stereo audio channels. An example of a matched microphone system is a product sold by Sound Professionals under the product designation SP-BMC-12. The speaker system of the remote control station may include headphones as shown in FIG. 1.

The robot 12 may also have a directional microphone 52. The directional microphone 52 can be used to capture sound received in a certain direction(s). For example, the directional microphone 52 may be a barrel-like structure that captures sound traveling along a desired axis but impedes off-axis sound. An example, of such a directional microphone is a product sold by Sennheiser under the product designation ME66/K6.

The robot 12 has a camera system. The camera system may include a first camera 54 and a second camera 56. The second camera 56 may include a zoom len(s) and is utilized when the system is in a zoom mode. The first camera 54 may provide images in a non-zoom mode. The system can be configured so that the sound captured by the directional microphone is the sole or primary sound recreated at the remote control station. Although two cameras are shown and described, it is to be understood that the robot may contain only one camera that has the capability to provide a zoom image and a non-zoom image.

The robot 12 may also have an antenna 58 that is wirelessly coupled to an antenna 60 of the base station 14. The system 10 allows a user at the remote control station 16 to move the robot 12 through operation of the input device 32. The robot cameras 54 and 56 are coupled to the remote monitor 24 so that a user at the remote station 16 can view a patient. Likewise, the robot monitor 40 is coupled to the remote camera 26 so that the patient can view the user. The microphones 28 and 48, 50 and 52, and speakers 30 and 44, allow for audible communication between the patient and the user.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

FIG. 2 shows an embodiment of a robot 12. Each robot 12 may include a high level control system 70. The high level control system 50 may include a processor 72 that is connected to a bus 74. The bus 74 is coupled to the cameras 54 and 56 by an input/output (I/O) ports 76 and 78, respectively. The monitor 40 is coupled to the bus 74 by a serial output port 80 and a VGA driver 82. The monitor 40 may include a touchscreen function that allows the patient to enter input by touching the monitor screen.

The microphones 48, 50 and 52 are coupled to the bus 74 by digital to analog converters 84, 86 and 88, respectively. The speaker 44 is coupled to the bus 74 by an analog to digital converter 90. The high level controller 70 may also contain random access memory (RAM) device 92, a non-volatile RAM device 94 and a mass storage device 96 that are all coupled to the bus 74. The mass storage device 96 may contain medical files of the patient that can be accessed by the user at the remote control station 16. For example, the mass storage device 96 may contain a picture of the patient. The user, particularly a health care provider, can recall the old picture and make a side by side comparison on the monitor 24 with a present video image of the patient provided by the camera 38. The robot antennae 58 may be coupled to a wireless transceiver 98. By way of example, the transceiver 98 may transmit and receive information in accordance with IEEE 802.11b.

The controller 70 may operate with a LINUX OS operating system. The controller 70 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control communication between the robot 12 and the remote control station 16.

The remote control station 16 may include a computer that is similar to the high level controller 50. The computer would have a processor, memory, I/O, software, firmware, etc. for generating, transmitting, receiving and processing information.

The high level controller 70 may be linked to a low level controller 100 by a serial port 102. The low level controller 100 runs software routines that mechanically actuate the robot 12. For example, the low level controller 100 provides instructions to actuate the movement platform to move the robot 12. The low level controller 52 may receive movement instructions from the high level controller 70. The movement instructions may be received as movement commands from the remote control station or another robot. Although two controllers are shown, it is to be understood that each robot 12 may have one controller, or more than two controllers, controlling the high and low level functions.

The robot 12 may have mechanisms so that the monitor 40, cameras 56 and 58 and microphones 48, 50 and 52 all move together in at least two degrees of freedom. Moving the microphones with the cameras insures that the microphone system provides stereophonic sound for all robot head positions. The system may be the same or similar to a robotic system provided by the assignee InTouch-Health, Inc. of Santa Barbara, Calif. under the name RP-6. The system may also be the same or similar to the system disclosed in U.S. Pat. No. 7,158,859 that issued on Jan. 2, 2007, which is hereby incorporated by reference.

Figure 3:
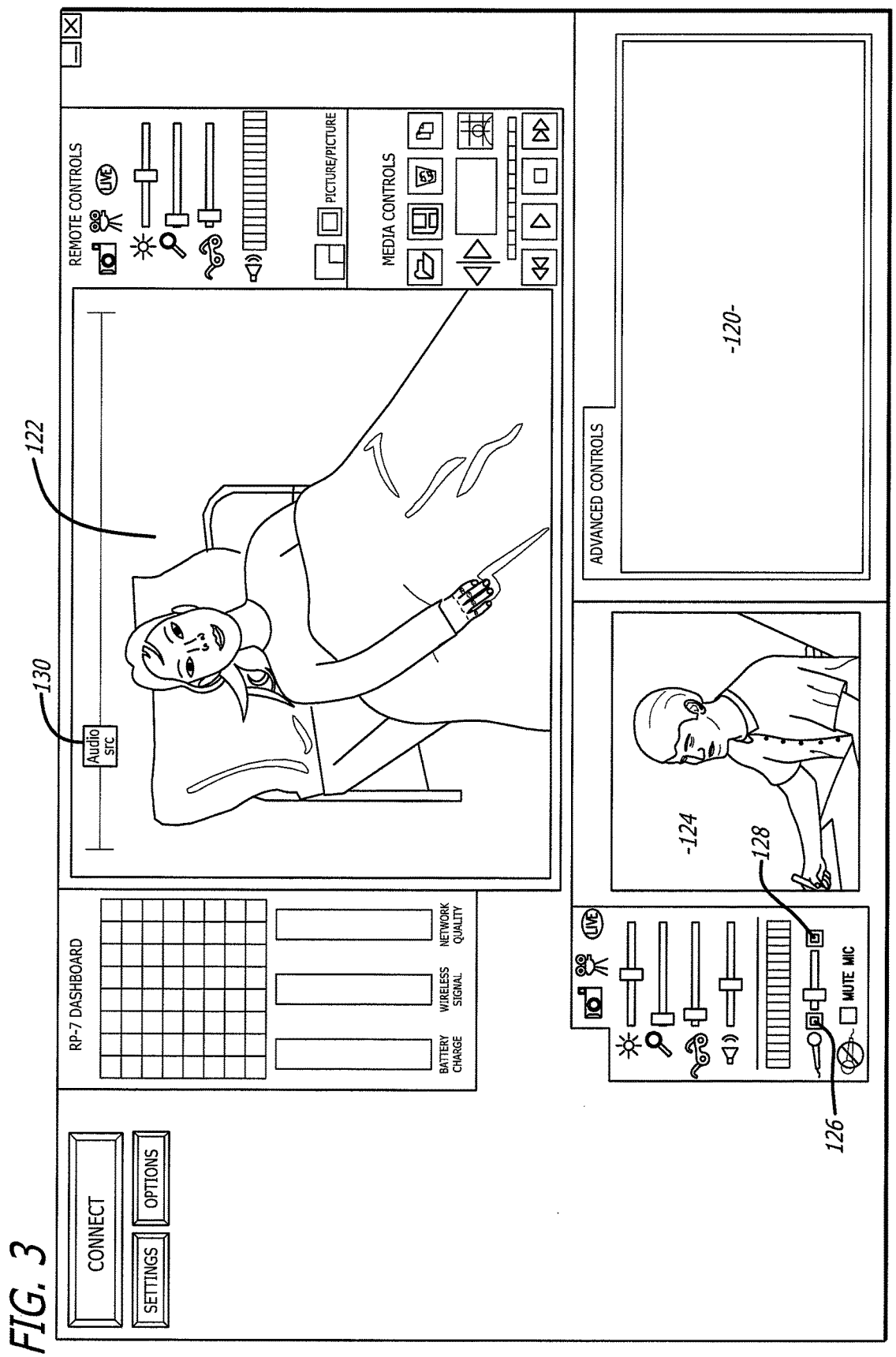
FIG. 3 is a graphical user interface of a remote station.

FIG. 3 shows a display user interface ("DUI") 120 that can be displayed at the remote station 16. The DUI 120 may include a robot view field 122 that displays a video image provided by the camera of the robot. The DUI 120 may also include a station view field 124 that displays a video image provided by the camera of the remote station 16. The DUI 120 may be part of an application program stored and operated by the computer 22 of the remote station 16.

The DUI 120 can include graphical icons 126 and 128 that allow the user to switch between the directional microphone and binaural microphone system, respectively. The DUI 120 may include a graphical overlay 130 in the robot view field 122 that indicates an origin of sound. The position of the overlay 130 corresponds to the sound origin. For example, the position of the overlay 130 shown in FIG. 3 indicates that the origin of sound is to the left of the robot. The user can then move the robot accordingly to improve the volume heard by the microphone system.

The origin of sound can be determined by initially looking at the time of difference between the arrival of sound to both microphones 48 and 50. The peak time $t_d$ can be found in the correlation function $C_{1,2}(t)=X_1(i)*X_2(i+t)$ for all i. An estimate for the angle of arrival (a) can be computed from the trig function $a=\arcsin(v*t_d/d_{1,2})$ where $d_{1,2}$ is the distance between microphones and v is the velocity of sound.

The system may have an automatic mode such that sound captured by the binaural microphone system is reproduced by the remote station when the camera system is in a non-zoom mode and sound captured by the directional microphone is reproduced by the station when the camera system is in a zoom mode. The user can switch between automatic and manual modes by selecting an icon (not shown). A letter "A" may appear adjacent to the icon when the system is in automatic mode. A letter "M" may appear when the system is in the manual mode.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or a facility by manipulating the input device 32 at a remote station 16. The robot 10 may be controlled by a number of different users. To accommodate for this the robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous tele-conference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables I and II, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user Notify requesting user that system is in use Set timeout | Warn current user of pending user Notify requesting user that system is in use Set timeout = 5 m | Warn current user of pending user Notify requesting user that system is in use Set timeout = 5 m Call back | Warn current user of pending user Notify requesting user that system is in use No timeout Call back |
| | Caregiver | Warn current user of pending user. Notify requesting user that system is in use. Release control | Not Allowed | Warn current user of pending user Notify requesting user that system is in use Set timeout = 5 m Queue or callback | Warn current user of pending user Notify requesting user that system is in use Set timeout = 5 m | Warn current user of pending user Notify requesting user that system is in use No timeout Callback |
| | Doctor | Warn current user of pending user Notify requesting user that system is in use Release control | Warn current user of pending user Notify requesting user that system is in use Set timeout = 5 m | Warn current user of pending user Notify requesting user that system is in use No timeout Callback | Notify requesting user that system is in use No timeout Queue or callback | Warn current user of pending user Notify requesting user that system is in use No timeout Callback |
| | Family | Warn current user of pending user Notify requesting user that system is in use Release Control | Notify requesting user that system is in use No timeout Put in queue or callback | Warn current user of pending user Notify requesting user that system is in use Set timeout = 1 m | Warn current user of pending user Notify requesting user that system is in use Set timeout = 5 m Queue or callback | Warn current user of pending user Notify requesting user that system is in use No timeout Callback |

TABLE II-continued

| | Requesting User | | | | |
|---|---|---|---|---|---|
| | Local | Caregiver | Doctor | Family | Service |
| Service | Warn current user of pending user<br>Notify requesting user that system is in use<br>No timeout | Notify requesting user that system is in use<br>No timeout<br>Callback | Warn current user of request<br>Notify requesting user that system is in use<br>No timeout<br>Callback | Warn current user of pending user<br>Notify requesting user that system is in use<br>No timeout<br>Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

The robot 12 and remote station 16 transmit commands through the broadband network 18. The commands can be generated by the user in a variety of ways. For example, commands to move the robot may be generated by moving the joystick 32 (see FIG. 1). The commands are preferably assembled into packets in accordance with TCP/IP protocol. Table III provides a list of control commands that are generated at the remote station and transmitted to the robot through the network.

TABLE III

| Control Commands | | |
|---|---|---|
| Command | Example | Description |
| drive | drive 10.0 0.0 5.0 | The drive command directs the robot to move at the specified velocity (in cm/sec) in the (x, y) plane, and turn its facing at the specified rate (degrees/sec). |
| goodbye | goodbye | The goodbye command terminates a user session and relinquishes control of the robot |
| gotoHomePosition | gotoHomePosition 1 | The gotoHomePosition command moves the head to a fixed "home" position (pan and tilt), and restores zoom to default value. The index value can be 0, 1, or 2. The exact pan/tilt values for each index are specified in robot configuration files. |
| head | head vel pan 5.0 tilt 10.0 | The head command controls the head motion. It can send commands in two modes, identified by keyword: either positional ("pos") or velocity ("vol"). In velocity mode, the pan and tilt values are desired velocities of the head on the pan and tilt axes, in degree/sec. A single command can include just the pan section, or just the tilt section, or both. |
| keepalive | keepalive | The keepalive command causes no action, but keeps the communication (socket) link open so that a session can continue. In scripts, it can be used to introduce delay time into the action. |
| odometry | odometry 5 | The odometry command enables the flow of odometry messages from the robot. The argument is the number of times odometry is to be reported each second. A value of 0 turns odometry off. |
| reboot | reboot | The reboot command causes the robot computer to reboot immediately. The ongoing session is immediately broken off. |
| restoreHeadPosition | restoreHeadPosition | The restoreHeadPosition functions like the gotoHomePosition command, but it homes the head to a position previously saved with gotoHomePosition. |
| saveHeadPosition | saveHeadPosition | The saveHeadPosition command causes the robot to save the current head position (pan and tilt) in a scratch location in temporary storage so that this position can be restored. Subsequent calls to "restoreHeadPosition" will restore this saved position. Each call to saveHeadPosition overwrites any previously saved position. |

TABLE III-continued

| | Control Commands | |
|---|---|---|
| Command | Example | Description |
| setCameraFocus | setCameraFocus 100.0 | The setCameraFocus command controls focus for the camera on the robot side. The value sent is passed "raw" to the video application running on the robot, which interprets it according to its own specification. |
| setCameraZoom | setCameraZoom 100.0 | The setCameraZoom command controls zoom for the camera on the robot side. The value sent is passed "raw" to the video application running on the robot, which interprets it according to its own specification. |
| shutdown | Shutdown | The shutdown command shuts down the robot and powers down its computer. |
| stop | stop | The stop command directs the robot to stop moving immediately. It is assumed this will be as sudden a stop as the mechanism can safely accommodate. |
| timing | Timing 3245629 500 | The timing message is used to estimate message latency. It holds the UCT value (seconds + milliseconds) of the time the message was sent, as recorded on the sending machine. To do a valid test, you must compare results in each direction (i.e., sending from machine A to machine B, then from machine B to machine A) in order to account for differences in the clocks between the two machines. The robot records data internally to estimate average and maximum latency over the course of a session, which it prints to log files. |
| userTask | userTask "Jane Doe" "Remote Visit" | The userTask command notifies the robot of the current user and task. It typically is sent once at the start of the session, although it can be sent during a session if the user and/or task change. The robot uses this information for record-keeping. |

Table IV provides a list of reporting commands that are generated by the robot and transmitted to the remote station through the network.

TABLE IV

| | Reporting Commands | |
|---|---|---|
| Command | Example | Description |
| abnormalExit | abnormalExit | This message informs the user that the robot software has crashed or otherwise exited abnormally. Te robot software catches top-level exceptions and generates this message if any such exceptions occur. |
| bodyType | bodyType 3 | The bodyType message informs the station which type body (using the numbering of the mechanical team) the current robot has. This allows the robot to be drawn correctly in the station user interface, and allows for any other necessary body-specific adjustments. |
| driveEnabled | driveEnabled true | This message is sent at the start of a session to indicate whether the drive system is operational. |
| emergencyShutdown | emergencyShutdown | This message informs the station that the robot software has detected a possible "runaway" condition (an failure causing the robot to move out of control) and is shutting the entire system down to prevent hazardous motion. |

TABLE IV-continued

Reporting Commands

| Command | Example | Description |
| --- | --- | --- |
| odometry | odometry 10 20 340 | The odometry command reports the current (x, y) position (cm) and body orientation (degrees) of the robot, in the original coordinate space of the robot at the start of the session. |
| sensorGroup | group_data | Sensors on the robot are arranged into groups, each group of a single type (bumps, range sensors, charge meter, etc.) The sensorGroup message is sent once per group at the start of each session. It contains the number, type, locations, and any other relevant data for the sensors in that group. The station assumes nothing about the equipment carried on the robot; everything it knows about the sensors comes from the sensorGroup messages. |
| sensorState | groupName state data | The sensorState command reports the current state values for a specified group of sensor. The syntax and interpretation for the state data is specific to each group. This message is sent once for each group at each sensor evaluation (normally several times per second). |
| systemError | systemError driveController | This message informs the station user of a failure in one of the robot's subsystems. The error_type argument indicates which subsystem failed, including driveController, sensorController, headHome. |
| systemInfo | systemInfo wireless 45 | This message allows regular reporting of information that falls outside the sensor system such as wireless signal strength. |
| text | text "This is some text" | The text string sends a text string from the robot to the station, where the string is displayed to the user. This message is used mainly for debugging. |
| version | version 1.6 | This message identifies the software version currently running on the robot. It is sent once at the start of the session to allow the station to do any necessary backward compatibility adjustments. |

The processor 72 of the robot high level controller 70 may operate a program that determines whether the robot 12 has received a robot control command within a time interval. For example, if the robot 12 does not receive a control command within 2 seconds then the processor 54 provides instructions to the low level controller 50 to stop the robot 12. Although a software embodiment is described, it is to be understood that the control command monitoring feature could be implemented with hardware, or a combination of hardware and software. The hardware may include a timer that is reset each time a control command is received and generates, or terminates, a command or signal, to stop the robot.

The remote station computer 22 may monitor the receipt of video images provided by the robot camera. The computer 22 may generate and transmit a STOP command to the robot if the remote station does not receive or transmit an updated video image within a time interval. The STOP command causes the robot to stop. By way of example, the computer 22 may generate a STOP command if the remote control station does not receive a new video image within 2 seconds. Although a software embodiment is described, it is to be understood that the video image monitoring feature could be implemented with hardware, or a combination of hardware and software. The hardware may include a timer that is reset each time a new video image is received and generates, or terminates, a command or signal, to generate the robot STOP command.

The robot may be a robot head that can both pivot and spin the camera 38 and the monitor 40. Such a head is described in the '859 patent. The robot head 350 may be in the system either with or instead of the mobile robot 12. The robot head can be particularly useful for doctor proctoring. The head can be located at a medical facility such as an emergency room or a doctor's office. A doctor at the remote location can assist in the diagnosis and medical treatment of a patient located at the robot location. The doctor can move the head to view the patient through control commands from the remote control station. Doctor proctoring can also be performed with a mobile robot 12.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A telepresence system, comprising:
a telepresence device with a camera, a monitor, a speaker, a plurality of microphones; and,
a remote station that transmits commands to control the telepresence device, the remote station includes a camera coupled to the telepresence device monitor, a monitor coupled to the telepresence device camera, a microphone coupled to the telepresence device speaker, and a speaker system that is coupled to one or more one or more of the telepresence device microphones, wherein the remote station monitor displays a display user interface with a graphical element that can be used to switch the remote station speaker system from reproducing sound from a first number of microphones of the telepresence device and a second number of microphones of the telepresence device, wherein both of the first and second numbers are greater than or equal to one and the first and second numbers are different.

2. The system of claim 1, wherein the telepresence device camera and the telepresence device microphones are attached to a robot head that can move in at least two degrees of freedom.

3. The system of claim 1, wherein the plurality of telepresence device microphones includes a first microphone and a second microphone that are spaced at approximately equal angles relative to a plane that intersects the telepresence device camera.

4. The system of claim 1, wherein the plurality of telepresence device microphones includes a directional microphone.

5. The system of claim 1, wherein the telepresence device camera can switch between zoom and non-zoom modes and the directional microphone is utilized when the camera system is in the zoom mode.

6. The system of claim 1, wherein the display user interface provides a graphical depiction of an origin of sound.

7. The system of claim 1, wherein the telepresence device includes a mobile platform.

8. A telepresence system, comprising:
a telepresence device with a camera, a monitor, a speaker, and a plurality of microphone systems that move together, the plurality of microphone systems includes a first microphone system having a first number of microphones and a second microphone system having a second number of microphones, wherein the first and second numbers are different; and,
a remote station that transmits commands to control the telepresence device, the remote station includes a speaker system that is coupled to at least one of the plurality of microphone systems of the telepresence device and a monitor coupled to the telepresence device camera, wherein the remote station monitor displays a display user interface that includes a graphical element that can be used to switch between the first and second microphone systems.

9. The system of claim 8, wherein one of the telepresence device microphone systems includes a first microphone located on a first side of the telepresence device camera and a second microphone located on a second side of the telepresence device camera.

10. The system of claim 9, wherein the first and second microphones are spaced at approximately equal angles relative to a plane that intersects the telepresence device camera.

11. The system of claim 8, wherein one of the telepresence device microphone system includes a directional microphone, the telepresence device camera can switch between a zoom mode and a non-zoom modes, and the directional microphone is utilized when said camera system is in said zoom mode.

12. The system of claim 8, wherein the display user interface provides a graphical depiction of an origin of sound.

13. The system of claim 8, wherein the telepresence device monitor is coupled to a camera of the remote station.

14. A method for hearing sound produced at a site of a telepresence device, comprising:
capturing sound with a number of microphones system of the telepresence device, the telepresence device including a camera system;
transmitting the sound to a remote station;
reproducing the sound at the remote control station; and,
displaying on a monitor of the remote station a display user interface that includes a graphical element that can be used to change the number of microphones of the telepresence device from which sound is reproduced at the remote station, where the number of microphones is at least one.

15. The method of claim 14, further comprising capturing the sound with a directional microphone.

16. The method of claim 15, further comprising switching the camera system of the telepresence device between zoom and non-zoom modes and producing the sound captured by the directional microphone when the camera system is in the zoom mode.

17. The method of claim 15, further comprising moving the telepresence device camera system and microphones in response to a command from the remote station.

18. The method of claim 14, wherein the display user interface provides a graphical depiction of an origin of sound.

* * * * *